US008586389B2

(12) United States Patent
Woolverton

(10) Patent No.: US 8,586,389 B2
(45) Date of Patent: Nov. 19, 2013

(54) LIGAND CONCENTRATING, LIQUID CRYSTAL BIOSENSOR SYSTEM

(75) Inventor: Christopher J. Woolverton, Kent, OH (US)

(73) Assignee: Kent State University, Kent, OH (US)

( * ) Notice: Subject to any disclaimer, the term of this patent is extended or adjusted under 35 U.S.C. 154(b) by 1329 days.

(21) Appl. No.: 11/535,562

(22) Filed: Sep. 27, 2006

(65) Prior Publication Data

US 2007/0099307 A1  May 3, 2007

Related U.S. Application Data

(60) Provisional application No. 60/596,487, filed on Sep. 28, 2005.

(51) Int. Cl.
*G01N 33/553* (2006.01)
*G01N 21/64* (2006.01)

(52) U.S. Cl.
USPC ........... 436/526; 436/518; 436/524; 436/525; 422/82.01; 422/98; 422/186.01; 422/186.04

(58) Field of Classification Search
USPC ......... 436/526, 518, 525, 524; 422/82.01, 98, 422/186.01, 186.04, 58; 204/403
See application file for complete search history.

(56) References Cited

U.S. PATENT DOCUMENTS

| | | | |
|---|---|---|---|
| 4,467,032 A | | 8/1984 | Lowke et al. |
| 6,013,531 A | * | 1/2000 | Wang et al. ................. 436/526 |
| 6,171,802 B1 | | 1/2001 | Woolverton et al. |
| 6,411,354 B1 | | 6/2002 | Lavrentovich |
| 6,548,311 B1 | * | 4/2003 | Knoll ........................... 436/524 |
| 6,797,463 B2 | | 9/2004 | Abbott et al. |
| 7,666,661 B2 | * | 2/2010 | Abbott et al. ............. 435/287.1 |
| 2003/0032039 A1 | | 2/2003 | Cunningham et al. |
| 2005/0048673 A1 | | 3/2005 | Baudry et al. |
| 2005/0112544 A1 | * | 5/2005 | Xu et al. ........................... 435/4 |
| 2007/0099249 A1 | * | 5/2007 | Abbott et al. ................. 435/7.5 |

OTHER PUBLICATIONS

Shiyanovskii et al. Real-time microbe detection based on director distortions around growing immune complexes in lyotropic chromonic liquid crystals. In: Phys Rev E, Feb. 2005, vol. 71, p. 020702-1 to 020702-4.

* cited by examiner

*Primary Examiner* — Mark Shibuya
*Assistant Examiner* — Pensee Do
(74) *Attorney, Agent, or Firm* — Hahn Loeser + Parks LLP; Scott M. Oldham, Esq.

(57) ABSTRACT

A method for detecting a ligand is provided. Antibodies to a predetermined ligand are attached to substrates. The substrates are superparamagnetic, dyed beads. The beads are exposed to an electromagnetic field to immobilize the beads. The beads are contacted with a sample and the antibodies are allowed to recognize and capture the ligand in the sample. The electromagnetic field is optionally removed. The beads are contacted with a liquid crystalline material and the light transmission properties of the liquid crystalline material are examined for alteration caused by the presence of aggregates of the beads and the ligand. A functional cassette for the detection of ligands comprises a pair of opposed, transparent substrates defining a space therebetween, a pair of transparent electrodes disposed on at least a portion of the opposed substrates on a side facing the opposing substrate and defining a primary detection area, and a secondary detection area adapted to capture aggregates of a ligand and ligand-recognizing antibodies attached to superparamagnetic, dyed beads. The detection areas are in fluid communication with each other.

25 Claims, 4 Drawing Sheets

LIGAND CONCENTRATING, LIQUID CRYSTAL BIOSENSOR SYSTEM

CROSS-REFERENCE TO RELATED APPLICATIONS/INCORPORATION BY REFERENCE

The present application claims priority from U.S. provisional application Ser. No. 60/596,487, filed Sep. 28, 2005. The disclosure of application Ser. No. 60/596,487 is hereby incorporated by reference.

TECHNICAL FIELD

This invention relates to the detection of a ligand by a receptor. More particularly, this invention relates to the detection of biologically relevant ligands, such as pathogenic microbes, using receptors attached to superparamagnetic particles or beads to capture the ligand.

BACKGROUND OF THE INVENTION

The detection of a ligand by a receptor (for example, detection of a pathogenic agent such as a microbe or toxin by an antibody; or detection of an antibody in blood by another antibody; or binding of a chemical toxin, such as nerve gas, to its receptor) is important in the diagnosis and treatment of individuals exposed to disease-causing or toxic agents. Early detection of pathogenic agents can be a great benefit in either disease prophylaxis or therapy before symptoms appear or worsen.

Every species, strain or toxin of a microbe contains unique surface ligands. Using molecular engineering and/or immunological techniques, receptor molecules, such as antibodies, can be isolated that will bind to these ligands with high specificity. Methods have also been developed where receptors, such as antibodies, are linked to a signaling mechanism that is activated upon binding.

Many available diagnostic tests are antibody-based, and can be used to detect either a disease-causing agent or a biologic product produced by the patient in response to the agent. There are currently three prevailing methods of antibody production for recognition of ligands (antigens): polyclonal antibody production in whole animals with recognition for multiple epitopes, monoclonal antibody production in transformed cell lines with recognition for a single epitope (after screening), and molecularly engineered phage displayed antibody production in bacteria with recognition of a single epitope (after screening). Each of these receptor systems is capable of binding and identifying a ligand, but the sensitivity of each is limited by the particular immunoassay detection system to which it is interfaced.

Immunoassays, such as enzyme-linked immunosorbent assay (ELISA), enzyme immunoassay (EIA), and radioimmunoassay (RIA), are well known for the detection of antigens. The basic principle in many of these assays is that an enzyme-, chromogen-, fluorogen-, or radionucleotide-conjugated antibody permits antigen detection upon antibody binding. In order for this interaction to be detected as a color, fluorescence or radioactivity change, significant numbers of antibodies must be bound to a correspondingly large number of antigen epitopes. The use of colorimetric assays using dyed beads with antibody receptors is also known. The use of magnetic beads having receptors to concentrate materials is also known in the biological art.

A system for detecting ligands which utilizes an amplification mechanism, such as an antibody-embedded liquid crystalline material, is provided by U.S. Pat. No. 6,171,802, the disclosure of which is incorporated herein by reference. It is also known that an electromagnetic field can be used to control the alignment of liquid crystalline materials. However, it has not been previously known to use superparamagnetic beads to concentrate a specific ligand within a liquid crystal-containing cassette for the purpose of ligand detection. Nor has it been previously known for a liquid crystal biosensor cassette to provide a second, confirmatory test.

SUMMARY OF THE INVENTION

It is therefore, an aspect of the present invention to provide a method and an apparatus for using receptor-coated superparamagnetic beads to concentrate and detect a specific ligand.

In general, the method of the present invention comprises a method of detecting a ligand by providing at least one receptor specific to the ligand, wherein the at least one receptor is attached to substrates to form receptor-bound substrates, exposing the substrates to an electromagnetic field to immobilize the substrates, contacting the substrates with a sample and allowing the receptors to recognize the ligand in the sample and form receptor-ligand complexes. Next, optionally, the electromagnetic field is removed, then contacting the beads with a liquid crystalline material and examining the light transmission properties of the liquid crystalline material for alteration caused by the presence of receptor-ligand complexes formed through the binding of ligands to the receptor-bound substrates.

The present invention also provides a functional cassette for the detection of ligands. The cassette includes a pair of opposed transparent substrates defining a space therebetween, a pair of transparent electrodes disposed on at least a portion of the opposed transparent substrates on a side facing the opposing substrate and defining a primary detection area and a secondary detection area adapted to capture receptor-ligand complexes comprising a ligand and a receptor, wherein the receptor is attached to spherical substrates to form a receptor-bound substrates, wherein the first detection area and the second detection area are in fluid communication with each other.

In another embodiment of the present invention, a functional cassette having a plurality of channels for the detection of ligands is provided. Each channel of the cassette includes a first front portion, wherein the front portion includes a sample application region, a second middle portion, wherein the second middle portion includes a pair of opposed transparent substrates defining a space therebetween and a pair of transparent electrodes disposed on at least a portion of the opposed transparent substrates on a side facing the opposing substrate and defining a primary detection area and a third end portion, wherein the third end portion includes a secondary detection area adapted to capture receptor-ligand complexes comprising a ligand and at least one receptor, wherein the at least one receptor is attached to substantially spherical substrates to form a receptor-bound substrates.

DETAILED DESCRIPTION OF THE INVENTION

Figure 1:
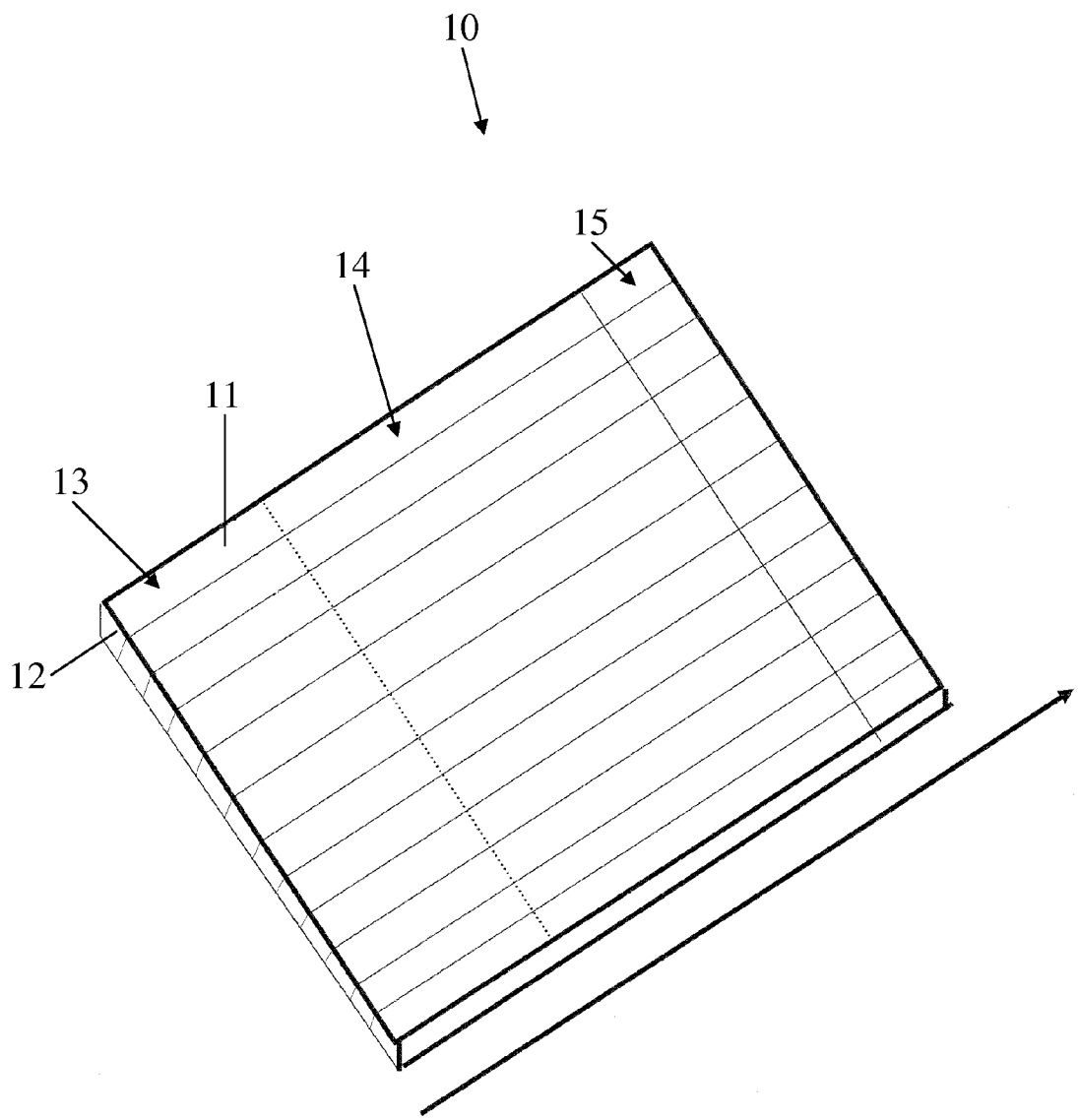
FIG. 1 illustrates a perspective view of the functional cassette according to the present invention.

As mentioned above, the present invention provides a device and method of detecting a ligand with a receptor for that ligand. In particular, the method includes inducing a magnetic field to capture paramagnetic receptor-coated substrates for binding to microbial ligands in a liquid crystalline material. The binding of the ligand to the receptor forms a birefringent receptor-ligand aggregate that yields a perceptible signal in the liquid crystalline material as a light transmissive signal.

Any receptor, such as antibodies or biologically engineered receptors for ligands, can be incorporated into the device as long as binding of the ligand to the receptor causes a detectable ligand aggregation and/or distortion (change in conformation) of the receptor. For example, any type of monospecific antibody (polyclonal, monoclonal, or phage displayed) can effectively function as a receptor and, thus, each of those antibody types will be described in the following paragraphs. Although phage-displayed antibodies can be expeditiously modified for identification of new ligands and are used as receptor examples in this patent application, any physically-distortable receptor-ligand interaction is appropriate for the detection component.

Antibody-based antigen detection has been exploited for several decades. Injection of a purified ligand (antigen) into a host animal stimulates the immune system to produce an array of antibodies against various reactive sites on the antigen. Since several lymphocytes are responding to different antigenic epitopes, a multi-specific antibody cocktail (polyclonal) is created and can be purified for antigen detection.

Antibody-producing spleen cells (B lymphocytes) are fused with immortalized myeloma cells to create hybridomas which provide nearly infinite quantities of antibody with a single, defined specificity. Interstrain and even interspecies hybrids of these 'monoclonal' antibodies can be generated through genetic engineering techniques. These highly specific antibodies have significant therapeutic potential, as evidenced by the U.S. Food and Drug Administration's approval of the use of mouse-human chimeric antibodies for treatment of selected diseases.

Phage-displayed techniques will be used to isolate single chain chimeric antibodies to various pathogenic agents. The genomic DNA of the B lymphocyte contains the code to produce an antibody to virtually all possible ligands (antigens). In a phage displayed antibody system (PDA), DNA encoding a single chain chimera of the native antibody:hypervariable ligand-binding region is synthesized by joining DNA encoding an antibody heavy chain and DNA encoding an antibody light chain and inserting therebetween DNA encoding a linker region. The desired amino acid sequence of the linker region depends on the characteristics required for any given amplification mechanism. The linker region may have to be able to interact and/or bond to a protein or other substance. Therefore, the polypeptide sequence may have to have, for example, a particular conformation, specifically placed functional groups to induce ionic or hydrogen bonds, or a hydrophobicity that is compatible with the amplification mechanism. Regardless of the type of amplification mechanism, however, the linker region plays a critical role in interfacing the amplification mechanism to the receptor.

An amplification mechanism including liquid crystalline material is utilized to amplify a receptor-ligand complex, thereby detecting the presence of ligands in a sample. A liquid crystal is a state of matter in which molecules exhibit some orientational order but little positional order. This intermediate ordering places liquid crystals between solids (which possess both positional and orientational order) and isotropic fluids (which exhibit no long-range order). Solid crystal or isotropic fluid can be caused to transition into a liquid crystal by changing temperature (creating a thermotropic liquid crystal) or by using an appropriate diluting solvent to change the concentration of solid crystal (creating a lyotropic liquid crystal). Both thermotropic and lyotropic liquid crystals can be used as the amplification mechanism of the device of the present invention. In one embodiment, a chromonic lyotropic liquid crystalline material is used as the amplification component of the device of the present invention.

Among these non-surfactant lyotropic liquid crystals are so-called lyotropic chromonic liquid crystals (LCLCs). The LCLC family embraces a range of dyes, drugs, nucleic acids, antibiotics, carcinogens, and anti-cancer agents. The LCLCs are fundamentally different from the better known surfactant-based lyotropic systems. Without limitation, one difference is that LCLC molecules are disc-like or plank-like rather than rod-like. The polar hydrophilic parts form the periphery, while the central core is relatively hydrophobic. This distinction creates a range of different ordered structures. Individual disc-like molecules may form cylindrical aggregates in water. The LCLCs are assumed to be formed by elongated aggregates, lamellar structures, and possibly by aggregates of other shapes.

Most lyotropic liquid crystals are formed using water as a solvent for biphilic molecules which possess polar (hydrophilic) parts and apolar (hydrophobic) parts. When water is added to biphilic molecules, a bilayer forms as the hydrophobic regions coalesce to minimize interaction with water while enhancing the polar component's interaction with water. The concentration and geometry of the specific molecules define the supramolecular order of the liquid crystal. The molecules can aggregate into lamellae as well as disk-like or rod-like micelles, or, generally, aggregates of anisometric shape. These anisometric aggregates form a nematic, smectic, columnar phase, of either non-chiral or chiral (cholesteric phase) nature. For example, the molecules form a stack of lamellae of alternating layers of water and biphilic molecules, thus giving rise to a lamellar smectic phase.

Lyotropic liquid crystals are usually visualized as ordered phases formed by rod-like molecules in water. A fundamental feature of the surfactant molecules is that the polar hydrophilic head group has an attached flexible hydrophobic tail. There is, however, a variety of other lyotropic systems that are not of the surfactant type, but which can also be successfully used in the present invention.

In one embodiment of the present invention, the cassette may include at least one substantially spherical substrate to which at least one receptor may be attached. The receptor or receptors that are attached to the spherical substrate are specific to a desired ligand to form a receptor-ligand complex such that, upon formation of said receptor-ligand complex, a detectable signal is produced in a liquid crystalline material. An amplification mechanism is interfaced with the receptor-ligand complex, where the amplification mechanism amplifies the signal produced by receptor-ligand complex formation in a liquid crystalline material. The substantially spherical substrate utilized in the present invention can be non-porous (solid) or porous. In one embodiment, the substantially spherical substrate is a solid sphere and the at least one receptor is attached to the outer surface of the spherical substrate.

In another embodiment, the substantially spherical substrate is porous. According to this embodiment, the at least one receptor may be attached to the surface of said porous substantially spherical substrate, the pores of said porous substantially spherical substrate, or both. By way of non-limiting example, if only one receptor is attached to the substantially spherical substrate, then the receptor can be attached to either the outer surface of the porous sphere or in the pores of the sphere. In an embodiment wherein more than one receptor is attached to the spherical substrate, all of the receptors can all be attached to only the outer surface of the sphere, or all the receptor can be attached within the pores of the sphere, or some receptors can be attached to the outer surface of the sphere and other receptors can be attached to the pores of the sphere. The use of a porous sphere or bead provides a greater surface area on which to attach receptors and, therefore, would also permit surface and luminal receptor-ligand interactions.

The receptors may be attached to the spherical substrate in any manner known in the art, including chemical attachment and physical attachment. In one embodiment, the receptors are attached to the spherical substrate by a chemical attachment, such as by covalent bonding to sulfate, amine, carboxyl or hydroxyl groups imbedded in the spherical substrate. However, it should be noted that the receptors wherein said at least one receptor is attached to said spherical substrate by any means of physical attachment.

The substantially receptor-coated spherical substrate is made from a material including, but not limited to, magnetic materials. In particular, the magnetic materials are a paramagnetic or a superparamagnetic material. The substantially receptor-coated spherical substrate may be colored with a dye in order to make it visually perceptible to colorimetric assays.

Paramagnetic materials are attracted to magnetic fields and are influenced by paramagnetism which is a form of magnetism which only occurs in the presence of an externally applied magnetic field. However, unlike ferromagnetic materials which are also attracted to magnetic fields, paramagnetic materials do not retain any magnetization in the absence of an externally applied magnetic field.

Constituent atoms or molecules of paramagnetic materials have permanent magnetic moments or dipoles, even in the absence of an applied field. This generally occurs due to the presence of unpaired electrons in the atomic/molecular electron orbitals. In pure paramagnetism, the dipoles do not interact with one another and are randomly oriented in the absence of an external field due to thermal agitation, resulting in zero net magnetic moment. When a magnetic field is applied, the dipoles will tend to align with the applied field, resulting in a net magnetic moment in the direction of the applied field. In the classical description, this alignment can be understood to occur due to a torque being provided on the magnetic moments by an applied field, which tries to align the dipoles parallel to the applied field.

Superparamagnetic materials are influenced by superparamagnetism which is a phenomenon by which magnetic materials may exhibit a behavior similar to paramagnetism even when at temperatures below the Curie or the Neel temperature, which is the temperature above which magnetic materials cease to exhibit spontaneous magnetization. This is observed in very fine particles, where the energy required to change the direction of the magnetic moment of a particle is comparable to the ambient thermal energy. At this point, the rate at which the particles will randomly reverse direction becomes significant.

Normally, coupling forces in ferromagnetic materials cause the magnetic moments of neighboring atoms to align, resulting in very large internal magnetic fields. This is what distinguishes ferromagnetic materials from paramagnetic materials. At temperatures above the Curie temperature (or the Neel temperature for antiferromagnetic materials), the thermal energy is sufficient to overcome the coupling forces, causing the atomic magnetic moments to fluctuate randomly. Since there is no longer any magnetic order, the internal magnetic field no longer exists and the material exhibits paramagnetic behavior. If the material is non-homogeneous, one can observe a mixture of ferromagnetic and paramagnetic clusters of atoms at the same temperature, i.e. superparamagnetic stage.

Superparamagnetism occurs when the material is composed of crystalline particles ranging in size from about 1-10 nm. In this case even when the temperature is below the Curie or Neel temperature (and hence the thermal energy is not sufficient to overcome the coupling forces between neighboring atoms), the thermal energy is sufficient to change the direction of magnetization of the entire crystallite. The resulting fluctuations in the direction of magnetization cause the magnetic field to average to zero. Thus the material behaves in a manner similar to paramagnetism, except that instead of each individual atom being independently influenced by an external magnetic field, the magnetic moment of the entire crystallite tends to align with the magnetic field.

The substantially receptor-coated spherical paramagnetic or superparamagnetic substrate may also include polymeric and inorganic materials. In one embodiment, the substantially receptor-coated spherical paramagnetic or superparamagnetic substrate may be coated with a polymeric material. Suitable polymeric materials which may comprise the spherical substrate include, but are not limited to, polyalkenes, polyacrylates, polymethacrylates, polyvinyls, polystyrenes, polycarbonates, polyesters, polyurethanes, polyamides, polyimides, polysulfones, polysiloxanes, polysilanes, polyethers, polycations, polyanions, and polycarboxylates. One particularly useful polymeric material used to manufacture the spherical substrate is polystyrene, especially when modified with copolymers of acrylic ester, chloromethylstyrene, methylamine, methyl methacrylate or made zwitterionic.

The liquid crystalline material that is utilized with the substantially coated spherical substrate includes all known types of thermotropic liquid crystalline materials and lyotropic liquid crystalline materials. In one preferred embodiment, lyotropic liquid crystalline material is used as the amplification mechanism. In another embodiment, lyotropic liquid crystalline materials of different origin, including surfactant and lyotropic chromonic liquid crystalline material, may used with the spherical substrate.

As described herein above, any receptor, such as antibodies or biologic/biologically engineered receptors for ligands, can be incorporated into the device as long as binding of the ligand to the receptor produces a detectable signal. Therefore, any type of monospecific antibody, including all polyclonal, monoclonal, or phage displayed antibodies can effectively function as a receptor.

An example of the device of the present invention may be described with reference to the FIGS. 1-4. The device may take form of a cassette 10 having one or more channels 11 between a pair of opposed substrates. As shown in the FIG. 1, the device is a multi-well cassette 10 having one or more channels 11. On a first end of the cassette, is a sample application region 12 for each channel 11. Each channel 11 of cassette 10 has a first front portion 13 that provides magnetic field; a second middle portion 14, wherein first front portion 13 and second middle portion 14 define a primary detection area for receptor-ligand complex formation through the observation of liquid crystal alignment distortion; and a third end portion 15 that provides a secondary detection area. The first detection area and second detection area are in fluid communication.

Figure 2:
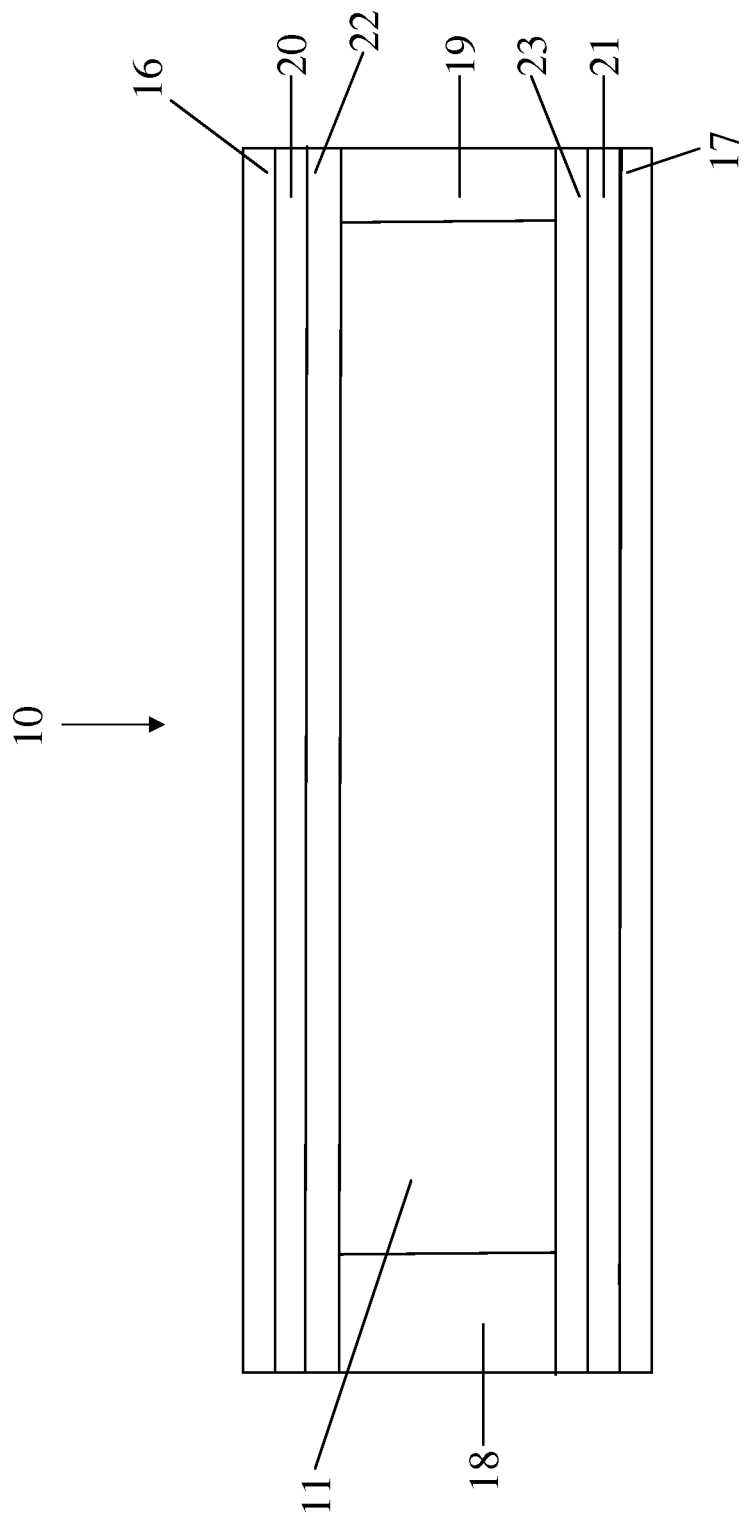
FIG. 2 shows a schematic view of the channel illustrated in FIG. 1.

As seen in FIG. 2, cassette 10 includes a pair of transparent substrates 16 and 17 separated by spacers 18 and 19. Cassette 10 also includes a pair of transparent electrodes 20 and 21, such as indium tin oxide (ITO) electrodes, disposed on opposing surfaces of substrates 16 and 17. Cassette 10 may also include polymer alignment layers 22 and 23 to enhance the interaction between the cassette-liquid crystal interactions.

Figure 3:
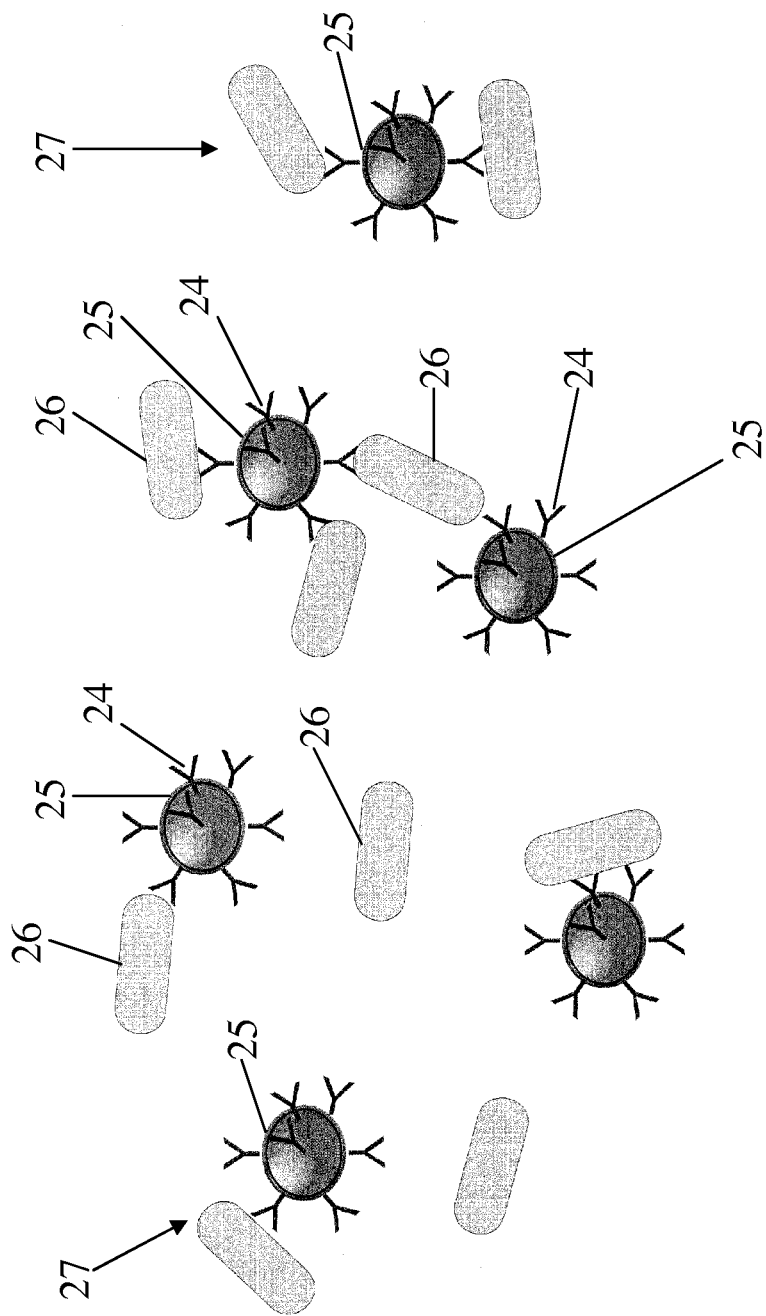
FIG. 3 is a schematic depiction of capture of ligand by the antibody coated superparamagnetic beads of the present invention.
Figure 4:
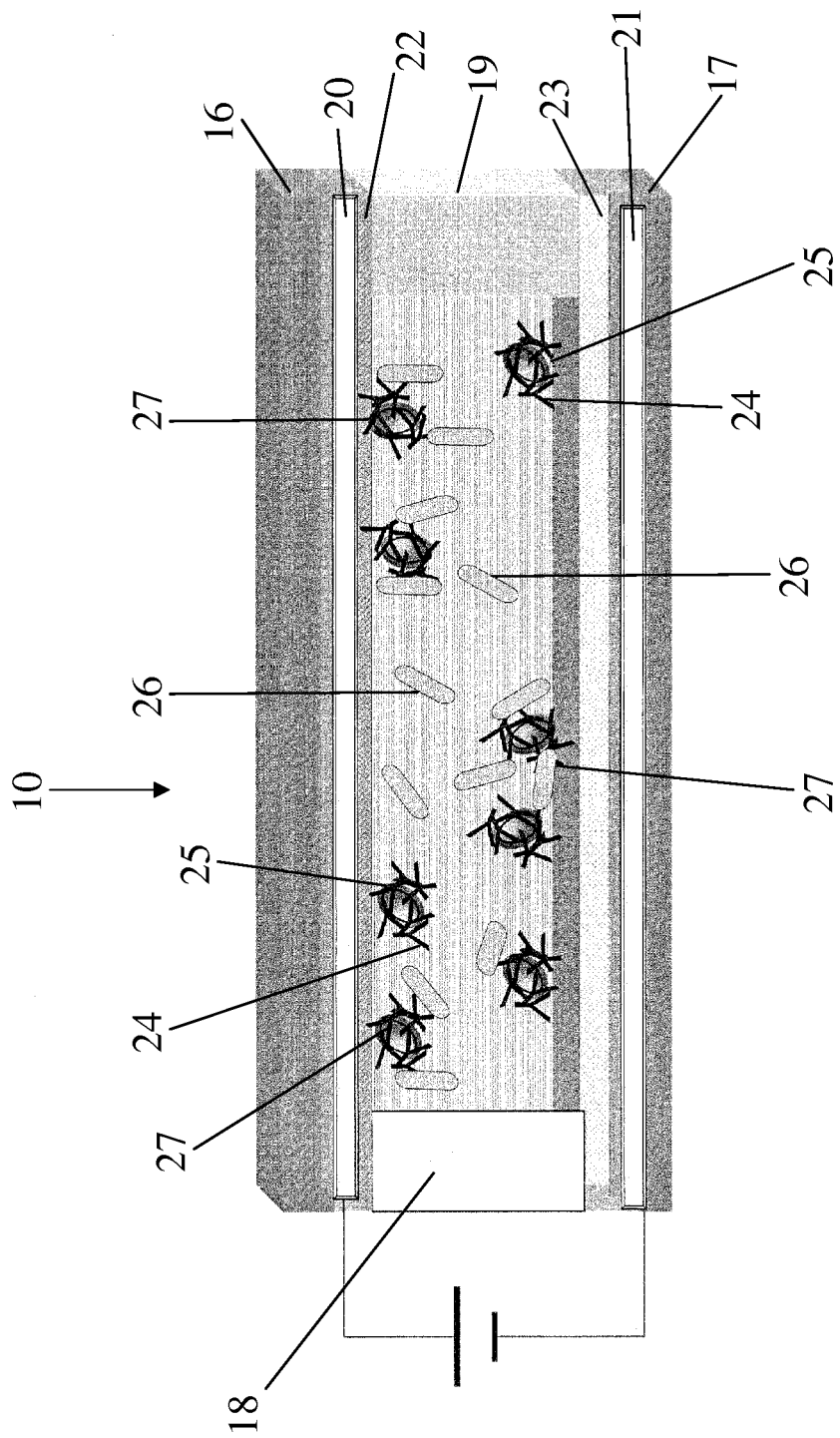
FIG. 4 is a schematic representation of superparamagnetic beads held in a magnetic field and capturing a ligand as it passes in the flow of a liquid crystalline material.

In one embodiment of the present invention, as seen in FIGS. 3 and 4, a receptor 24 is attached to a substrate 25. Substrate 25, for example, is a superparamagnetic, dyed bead. Typically, the receptor 24 will be an antibody raised against a specific, complimentary ligand 26. In each channel 11, the receptor-bound substrates 25 are introduced and temporarily immobilized by an electromagnetic field, such as one produced by electrodes 20 and 21 on a pair of opposed, transparent substrates 16 and 17. In another embodiment of the present invention, a portable, handheld magnetic device, capable of producing a electromagnetic field, may be employed to further assist in the temporary immobilization of the receptor-bound substrates 25 that have been subjected to the electromagnetic field produced by electrodes 20 and 21 on the pair of opposed, transparent substrates 16 and 17.

Once immobilized, the receptor-bound substrates 25 are then exposed to a sample that is introduced into sample application region 12 and travels to front portion 13 of cassette 10 where it comes in contact with the receptor-bound substrates 25. If the ligand 26 is present in the sample, it can bind to the antibody or other receptor 24 to form a receptor-ligand complex 27. The ligand may be, for example a particular microbe. Since the receptor-bound substrates 25 are immobilized, a relatively large volume of sample may be permitted to flow over the receptor-bound substrates 25, thereby concentrating the ligand 26. A liquid crystalline material can then be introduced into channel 11.

The magnetic field may then be released, permitting further aggregation of receptor-bound substrates 25 and ligands 26 in the liquid crystalline material as it travels down through the middle portion 14 of cassette 10 thus forming a network of receptor-modified substrates 25 and ligands 26 which are moveable within the liquid crystalline material. The formation of the receptor-ligand complex 27 may be detected by the alteration of the light transmission properties of a liquid crystalline material. This detection may be accomplished, when the magnetic field is released, by distortion of the alignment of the liquid crystal material in bulk. A polymer alignment layer 22 and/or 23, if provided on a portion of one or both of the transparent substrates 16 and 17, aids in the examination of the light transmission properties of the liquid crystalline material.

When the magnetic field is not released, the receptor-ligand complex 27 may still alter the alignment, and therefore, the light transmission properties, of the liquid crystalline material. Liquid crystals are anisometric molecules that exhibit limited chemical interaction but that tend to orient along a common direction (the director). Director orientation is affected by externally applied fields (electrical and magnetic); at the boundary between the liquid crystal and the container and flow. The liquid crystal orientation was optimized by constructing glass assay chambers that enhanced container-liquid crystal interaction.

Following examination of the light transmission properties of the liquid crystal, the receptor-ligand complexes 27 in the liquid crystalline material may flow to the end portion 15 of cassette 10 where a secondary detection method may be employed. In one embodiment, the secondary method includes capture of the receptor-ligand complexes 27 by a second antibody raised against the receptor-ligand complexes 27. When a second antibody or other receptor is used, it may be bound to a substrate to form a secondary, solid phase binding site, where aggregates of ligand and bead are selectively bound. The secondary detection method thus confirms identity specificity.

In another embodiment of the present invention, receptor-ligand complexes 27 can be retained on a filter, for example. When the filter is used, it should retain receptor-ligand complexes 27, while allowing individual substrates 25, ligands 26 or other test components to pass through the filter. In either case, accumulation of the dyed substrates 25 may be detected calorimetrically.

Based upon the foregoing disclosure, it should now be apparent that cassette of the present invention will carry out the objects set forth hereinabove. It is, therefore, to be understood that any variations evident fall within the scope of the claimed invention and thus, the selection of specific component elements can be determined without departing from the spirit of the invention herein disclosed and described.

What is claimed is:

1. A functional cassette for the detection of ligands, the cassette comprising:
   a pair of opposed transparent substrates defining a space therebetween;
   a liquid crystalline material disposed within the space defined by the pair of opposed transparent substrates;
   a pair of transparent electrodes disposed on at least a portion of the opposed transparent substrates on a side facing the opposing substrate and defining a primary detection area, wherein the primary detection area includes a liquid crystalline material and a plurality of receptors specific to a ligand, wherein the plurality of receptors are attached to substrates to form receptor-bound substrates, and a sample for analysis can be introduced therein, such that any ligands in the sample form receptor-ligand complexes upon binding of the ligands to the receptor-bound substrates, wherein the formation of receptor-ligand complexes may be detected by alteration of the light transmission properties of the liquid crystalline material in the primary detection area; and
   a secondary detection area adapted to detect aggregated receptor-ligand complexes located within the liquid crystalline material by a secondary detection method, wherein the primary detection area and the secondary detection area are in fluid communication with each other.

2. The cassette of claim 1, wherein the receptor is attached to a plurality of magnetic substrates are superparamagnetic.

3. The cassette of claim 2, wherein the substrates are selected from the group of dyed, superparamagnetic, or combinations thereof.

4. The cassette of claim of claim 1, wherein the substrates are superparamagnetic and dyed.

5. The cassette of claim 1, wherein the receptor is an antibody.

6. The cassette of claim 1, wherein the pair of transparent electrodes are capable of producing a magnetic field to aggregate the receptor-bound substrates.

7. The cassette of claim 6, wherein the pair of transparent electrodes comprise indium tin oxide.

8. The cassette of claim 1, wherein a portion of at least one of the pair of transparent substrates are coated with a polymer alignment layer.

9. The cassette of claim 1, wherein the secondary detection area further comprises a second receptor raised against the receptor-ligand complexes.

10. The cassette of claim 9, wherein the second receptor confirms identity specificity of the receptor-ligand complexes.

11. The cassette of claim 1, wherein the secondary detection area includes a filter.

12. The cassette of claim 1, wherein the liquid crystalline material is selected from the group consisting of a thermotropic liquid crystalline material and a lyotropic liquid crystalline material.

13. The cassette of claim 12, wherein the lyotropic liquid crystalline material is a lyotropic chromonic liquid crystalline material.

14. A functional cassette for the detection of ligands comprising:
a pair of opposed transparent substrates defining a space therebetween, wherein a liquid crystalline material and a plurality of receptors specific to a ligand, wherein the plurality of receptors are attached to substrates to form receptor-bound substrates, are disposed within the space defined by the pair of opposed transparent substrates, and a pair of transparent electrodes disposed on at least a portion of the opposed transparent substrates on a side facing the opposing substrate wherein the cassette allows for a sample for analysis to be introduced therein, such that any ligands in the sample form receptor-ligand complexes upon binding of the ligands to the receptor-bound substrates and allows for a primary detection by alteration of the light transmission properties of the liquid crystalline material in a primary detection area, and a secondary detection area to detect of aggregated receptor-ligand complexes formed in the liquid crystalline material by a secondary detection method.

15. The cassette of claim 14, wherein the receptor is attached to a plurality of magnetic substrates are superparamagnetic.

16. The cassette of claim 15, wherein the substrates are selected from the group of dyed, superparamagnetic, or combinations thereof.

17. The cassette of claim of claim 14, wherein the substrates are superparamagnetic and dyed.

18. The cassette of claim 14, wherein the receptor is an antibody.

19. The cassette of claim 14, wherein the pair of transparent electrodes are capable of producing a magnetic field to immobilize the receptor-bound substrates.

20. The cassette of claim 19, wherein the pair of transparent electrodes comprise indium tin oxide.

21. The cassette of claim 14, wherein a portion of the transparent electrodes are coated with a polymer alignment layer.

22. The cassette of claim 14, wherein the secondary detection area further comprises a second receptor raised against the receptor-ligand complexes.

23. The cassette of claim 22, wherein the second receptor confirms identity specificity of the receptor-ligand complexes.

24. The cassette of claim 14, wherein the liquid crystalline material is selected from the group consisting of a thermotropic liquid crystalline material and a lyotropic liquid crystalline material.

25. The cassette of claim 24, wherein the lyotropic liquid crystalline material is a lyotropic chromonic liquid crystalline material.

* * * * *